(12) United States Patent
Hui et al.

(10) Patent No.: US 11,026,602 B2
(45) Date of Patent: Jun. 8, 2021

(54) SYSTEM FOR HEARING SENSITIVITY TESTING AND AUTO REINFORCEMENT

(71) Applicant: BITwave Pte Ltd, Singapore (SG)

(72) Inventors: Siew Kok Hui, Singapore (SG); Leon Shi Terng Tan, Singapore (SG)

(73) Assignee: BITWAVE PTE LTD, Singapore (SG)

(*) Notice: Subject to any disclaimer, the term of this patent is extended or adjusted under 35 U.S.C. 154(b) by 573 days.

(21) Appl. No.: 14/854,718

(22) Filed: Sep. 15, 2015

(65) Prior Publication Data
US 2016/0081595 A1 Mar. 24, 2016

Related U.S. Application Data

(60) Provisional application No. 62/052,754, filed on Sep. 19, 2014.

(51) Int. Cl.
*A61B 5/12* (2006.01)

(52) U.S. Cl.
CPC .................................. *A61B 5/123* (2013.01)

(58) Field of Classification Search
None
See application file for complete search history.

(56) References Cited

U.S. PATENT DOCUMENTS

| | | | | |
|---|---|---|---|---|
| 5,729,658 A * | 3/1998 | Hou | ...................... | G10L 25/69 381/60 |
| 5,825,894 A * | 10/1998 | Shennib | ................. | G16H 40/40 381/60 |
| 6,167,138 A * | 12/2000 | Shennib | ................. | G16H 40/40 381/60 |
| 7,187,778 B2 * | 3/2007 | Basseas | ............. | G05B 13/0285 381/314 |
| 9,489,854 B2 * | 11/2016 | Haruta | ...................... | G09B 5/00 |
| 2006/0167335 A1 * | 7/2006 | Park | ....................... | A61F 11/00 600/25 |
| 2008/0187145 A1 * | 8/2008 | Burrows | ................ | A61B 5/121 381/60 |
| 2009/0220099 A1 * | 9/2009 | Voix | ..................... | H04R 29/004 381/59 |
| 2010/0111316 A1 * | 5/2010 | Voix | ....................... | H04R 25/70 381/60 |
| 2010/0257128 A1 * | 10/2010 | De Vries | ................ | G06N 20/00 706/12 |
| 2013/0343583 A1 * | 12/2013 | Marcoux | ............... | G16H 20/30 381/314 |

(Continued)

*Primary Examiner* — Patrick Fernandes
*Assistant Examiner* — Benjamin S Melhus
(74) *Attorney, Agent, or Firm* — Amin, Turocy & Watson, LLP

(57) ABSTRACT

Disclosed is a graphical user interface operational on a portable device that allows users to test their minimum audio hearing level at various frequencies using a single button. The graphical user interface generates sound frequencies that are played to the user, one ear at a time. Starting from zero decibels, sound intensity levels are gradually increased to intensity levels perceptible by the user. The users indicate recognition of the sound frequency by interacting with the graphical user interface. The intensities of the sound pressure levels (SPLs) are registered as estimates of a user's hearing sensitivity at the tested frequency bands. The process is repeated at different frequency bands for each ear, and hearing levels for each ear established.

20 Claims, 10 Drawing Sheets

(56) References Cited

U.S. PATENT DOCUMENTS

| | | | |
|---|---|---|---|
| 2014/0194775 A1* | 7/2014 | Van Hasselt | A61B 5/121 |
| | | | 600/559 |
| 2014/0219486 A1* | 8/2014 | Brown | A61N 1/36038 |
| | | | 381/320 |
| 2014/0309549 A1* | 10/2014 | Selig | H04R 1/1041 |
| | | | 600/559 |
| 2015/0073296 A1* | 3/2015 | Zeng | A61B 5/128 |
| | | | 600/559 |
| 2015/0208956 A1* | 7/2015 | Schmitt | A61B 5/123 |
| | | | 600/559 |

\* cited by examiner

SYSTEM FOR HEARING SENSITIVITY TESTING AND AUTO REINFORCEMENT

CROSS REFERENCE TO RELATED APPLICATIONS

This application claims the benefit of priority to the filing date of U.S. Provisional Application Ser. No. 62/052,754, filed Sep. 19, 2014, and entitled "SYSTEM FOR HEARING SENSITIVITY TESTING AND AUTO RE-ENFORCEMENT". The content of the foregoing provisional application is hereby incorporated herein by reference in its entirety.

TECHNICAL FIELD

The subject disclosure relates to hearing sensitivity testing and auto reinforcement.

BACKGROUND

Hearing loss is not just a phenomenon suffered solely by an aging demographic, many young people now suffer the same problem due to prolonged exposure to loud sounds, especially from their headphones and/or headsets while listening to music on mobile devices. Due to the popularity of portable audio devices, such as MP3 players and smart phones, many young people today suffer from severe hearing loss due to prolonged exposure to excessively loud music and/or noise, because the younger demographic tend to set the volume/intensity level of their portable devices too high while listening through their headsets or headphones; this is particularly the case in noisy environments, such as on commuter trains and buses, in bus stations, train stations, and airports, as well as in shopping malls, to name but a few.

SUMMARY

The following presents a simplified summary of the disclosure in order to provide a basic understanding of some aspects of the disclosure. This summary is not an extensive overview of the disclosure. It is intended to neither identify key or critical elements of the disclosure nor delineate any scope of the particular aspects of the disclosure, or any scope of the claims. Its sole purpose is to present some concepts of the disclosure in a simplified form as a prelude to the more detailed description that is presented later.

In accordance with one or more implementations of the disclosure, various non-limiting aspects are described in connection with a system and/or method for hearing sensitivity testing and auto re-enforcement. For instance, in accordance with a non-limiting implementation, presented are systems and/or methods in which a processor, and a memory that stores executable instructions that, when executed by the processor, facilitate performance of operations comprising: generating sine tones representing audible frequencies within one or more defined bands of audible frequencies, propagating the generated sine tones to auditory organs of a user, and in response to receiving input from the user, determining minimum intensities of the generated sine tones as recognized by the user.

The following description and the annexed drawings set forth certain illustrative aspects of the disclosure. These aspects are indicative, however, of but a few of the various ways in which the principles of the disclosure may be employed. Other advantages and novel features of the disclosure will become apparent from the following detailed description of the disclosure when considered in conjunction with the drawings.

DETAILED DESCRIPTION

Figure 1:
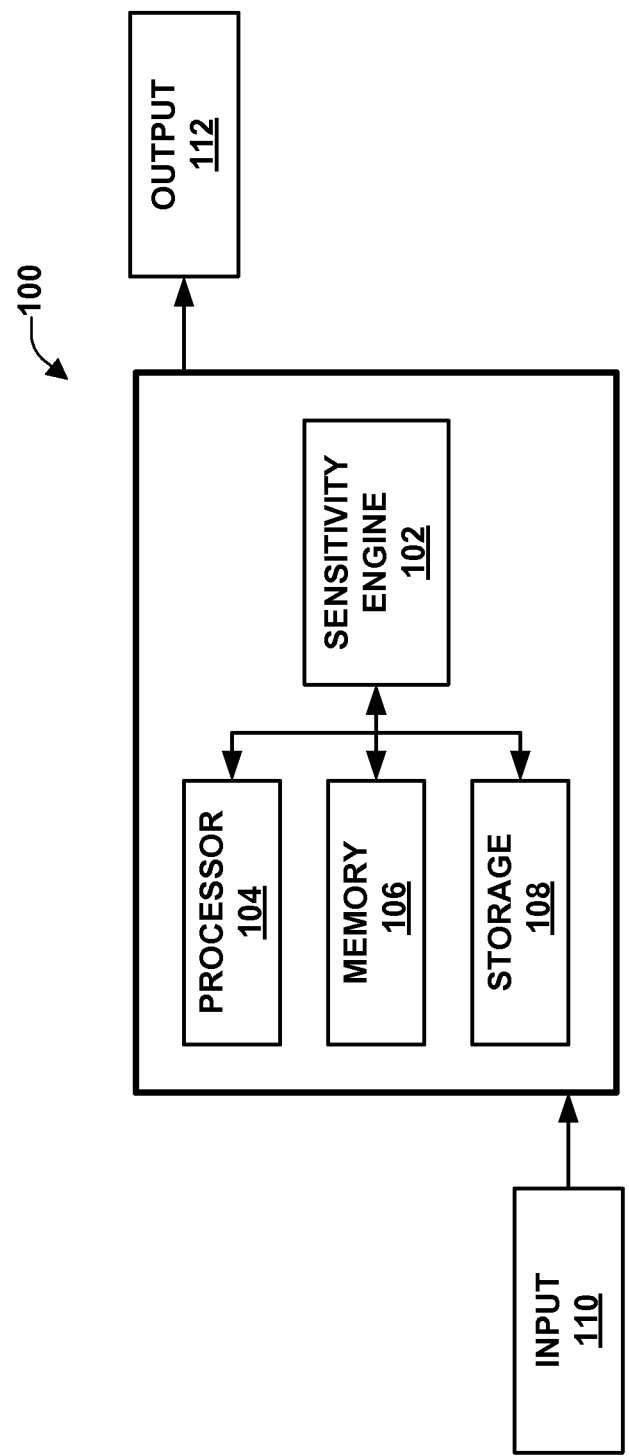
FIG. 1 illustrates an example non-limiting system that facilitates hearing sensitivity testing and auto reinforcement, in accordance with various aspects and implementations described herein.

The subject disclosure is now described with reference to the drawings, wherein like reference numerals are used to refer to like elements throughout. In the following description, for purposes of explanation, numerous specific details are set forth in order to provide a thorough understanding of this disclosure. It may be evident, however, that the subject disclosure can be practiced without these specific details. In other instances, well-known structures and components are shown in block diagram form in order to facilitate describing the subject disclosure.

It is to be appreciated that in accordance with one or more aspects or implementations described in this disclosure, users can opt-out of providing personal information, demographic information, location information, proprietary information, sensitive information, or the like in connection with data gathering aspects. Moreover, one or more aspects or implementations described herein can provide for anonymizing collected, received, or transmitted data.

As noted above, hearing loss is not a phenomena confined to the elderly, an ever younger demographic is now also experiencing significant hearing loss due to playing music, at significant and deleteriously enhanced intensity (volume)

levels and for prolonged durations of time, through headphones or headsets connected to electronic devices capable of playing digital audio files and/or broadcast programs, such as laptops, notebook computers, tablet computers, desktop computers, smart phones, mobile devices, industrial and/or consumer electronic devices, and the like.

To date, measuring hearing sensitivity of individuals has only been possible using specialized audiological equipment, such as specifically designed headphones or headsets with embedded acoustic sensors operated by trained professionals, such as audiologists. Needless to say, access to such specialized equipment operated by specialists in the field of audiology can be expensive and typically is cost prohibitive for most people, especially the young. Thus, by the time hearing loss is ultimately detected, severe and irreversible damage can have already been done.

In view of the foregoing therefore, disclosed is a device, comprising a processor; and a memory that stores executable instructions that, when executed by the processor, facilitate performance of operations. The operations can comprise generating a first sine tone representing a first audible frequency within a defined band of audible frequencies, wherein the first sine tone represents a center frequency in the first defined band of audible frequencies; propagating the first sine tone to a first auditory organ (e.g., right ear) of a user; and in response to receiving input from the user, determining a minimum intensity of the first sine tone recognized by the user.

Additional operations performed by the processor can include incrementally increasing an intensity of the first sine tone until the user indicates recognition of the first sine tone; and propagating the first sine tone to a second auditory organ (e.g., left ear) of the user. Further operations can also include generating a second sine tone representing a second audible frequency in the defined band of audible frequencies; propagating the second sine tone to the first auditory organ of the user; and propagating the second sine tone to a second auditory organ of the user. In the context of the foregoing, the defined band is a first defined band and as such the operations can further comprise, in response to receiving input from the user, generating a third sine tone representing a third audible frequency in a second defined band of audible frequencies; propagating the third sine tone to the first auditory organ of the user; propagating the third sine tone to a second auditory organ of the user; and as a function receiving responses from the user for sine tones representing audible frequencies comprising a set of defined bands of audible frequencies for the first auditory organ, determining a set of parameters representing respective signal levels and gain settings for the set of defined bands of audible frequencies.

In accordance with a further embodiment, the subject disclosure describes a method, comprising a series of acts that include: generating a first sine tone representing an audible frequency; propagating the first sine tone to a first sound sensor of a user; increasing an intensity level of the first sine tone from a first intensity level to a second intensity level; and as a function of the second intensity level, determining for the first sound sensor of the user, a set of parameters representing respective signal levels or respective gain settings for sine tones representing audible frequencies in a defined band of frequencies. The second intensity level is the intensity level of the first sine tone that the user is determined to have recognized as being perceptible, and the first sine tone represents a center frequency in the audible frequency.

Further acts can include: after the first sine tone has been propagated to the first sound sensor of the user, generating a second sine tone representing another audible frequency; propagating the second sine tone to a second sound sensor of a user; increasing an intensity level of the second sine tone from a third intensity level to a fourth intensity level; and as a function of the fourth intensity level, determining for the second sound sensor of the user, another set of parameters representing respective other signal levels or respective other gain settings for other sine tones representing other audible frequencies in another defined band of frequencies.

In accordance with a still further embodiment, the subject disclosure describes a machine-readable storage medium, comprising executable instructions that, when executed by a processor, facilitate performance of operations, comprising: generating a first sine tone representing an audible frequency; propagating the first sine tone, via a first electro-acoustic transducer, to a first ear associated with a user identity; increasing an intensity level of the first sine tone, supplied via the electro-acoustic transducer to the first ear, from a first intensity level to a second intensity level; and determining, for the first ear of the user and as a function of the second intensity level, parameters representing a signal level or a gain setting for each sine tone representing each audible frequency in a defined band of frequencies.

Further operations can include: after each sine tone representing each audible frequency in the defined band of frequencies has been propagated to the first ear of the user, generating a third sine tone representing another audible frequency; propagating the third sine tone, via a second electro-acoustic transducer, to a second ear associated with the user identity; increasing, by the system, another intensity level of the second sine tone from a third intensity level to a fourth intensity level; and determining, for the second ear associated with the user identity and as a function of the fourth intensity level, other parameters representing another signal level or another gain setting for each other sine tone representing each other audible frequency in another defined band of frequencies. The first ear can be a right ear of the user and the second ear can be a left ear of the user.

In accordance with an additional and/or alternative embodiment, the subject application describes a graphical user interface that can execute on a device that includes or comprises at least a processor and a memory that stores executable instructions that, when executed by the processor facilitate performance of operations. The operations allow users to test their minimum audio hearing level at various frequencies using a single button associated with the device. The frequency ranges can be divided into defined numbers of frequencies or frequency bands in a psychoacoustical scale, such as the Bark Scale, mel scale, and the like.

In accordance with an aspect, certain sound frequencies can be played to each ear, auditory organ, or auditory sensor (should the user employ auditory enhancement devices) of the user, one ear at a time. Starting from zero decibel, the sound intensity for a selected frequency band can be gradually and incrementally increased. When the volume/intensity of the sound in the selected frequency band approaches the user's audible range (e.g., the user initially hears the sound), the user can indicate recognition of the propagated sound at the selected frequency and at the sound intensity/volume by clicking a button that can be displayed on an associated display device, for instance. The intensity/volume of the propagated sound. SPL (sound pressure level) can then be registered as an estimate of the user's hearing level at the selected sound frequency band and the sound intensity/ volume. The foregoing process can be repeated for different defined frequency bands and with respect to each ear of the user, one ear at a time.

In accordance with a further embodiment, the subject disclosure provides a user interface operable on any portable device, such as a mobile cellular device, smartphone device, laptop device, tablet computer device, and the like, through connected headset or headphone devices, to be configured to be a hearing sensitivity measurement device, and/or configured for providing hearing sensitivity measurement. In accordance with an aspect, the portable device can be configured to facilitate execution of one or more computer or machine operations to cause a graphical user interface (GUI) to interact with an audio and transport layer application programming interface (API) that can typically be supplied by portable device manufacturers. The graphical user interface in conjunction with the underlying audio and transport layer application programming interface can permit versatile hardware configurations. For example, a graphical user interface can be configured to be operational with a headset that is wirelessly coupled with the portable device (e.g., via Bluetooth) as well as with headphones that are coupled directly through wire to the portable device.

In accordance with yet further embodiments, the subject application discloses a technique or process that is based on iterative incremental refinements of an intensity level of an output signal generated and propagated to each ear (e.g., auditory sensory organ, auditory enhancement device, . . . ) of a user via wired and/or wireless headsets or headphones coupled to a portable device. Such iterative and/or incremental refinements of the intensity level of an output signal generated for different audio frequencies bands within a defined ranges, spectrums, or scales of audible sound frequencies can allow users to discover the minimum perceptible level of their hearing sensitivity at the different audio frequencies within disparate and distinct ranges, spectrums, or scales of audible sound frequencies.

Moreover, and as a function of a detected minimum perceptible level, a set of parameters can be determined. The set of parameters can be representative of the hearing responses of the user wherein the set of parameters can be employed to generate (e.g., plot) and display hearing curve(s) on a display device associated with the portable device. It will be noted in relation to the generation and displaying of the hearing curve(s) that, in accordance with an aspect, the generated and displayed hearing curve(s) can be generated within the described graphical user interface. Additionally, the set of derived parameters can also be employed or utilized to tune parameters or coefficients for hearing aid filter designs, for example.

Further in accordance with an embodiment and through use of the facilities provided by the systems and/or method disclosed herein, sets of derived parameters can be generated from a representative cross section of a demographic in order to determine or ascertain a normalized hearing sensitivity level (e.g., a range of hearing sensitivity) for the identified demographic. For instance, the identified demographic can be identified, for instance, as a function of age, sex, profession, and the like. The normalization of the hearing sensitive level can be determined as a statistical average, mean, modal, and/or median value(s) of the sets of derived parameters determined across the identified demographic. Thus, by comparing a user's set of derived and generated hearing parameters against the average, statistical average, mean, modal, and/or median value(s) for the identified demographic, an assessment can be made in regard to an individual user's hearing sensitivity in relation to the hearing sensitivity levels of the identified demographic.

Turning now to the drawings, with reference initially to FIG. 1, a non-limiting depiction of a system for hearing sensitivity testing and auto reinforcement, in accordance with an aspect. As depicted in FIG. 1, system 100 can be any type of mechanism, machine, device, facility, and/or instrument that includes a processor and/or is capable of effective and/or operative communication with a network topology. Illustrative mechanisms, machines, devices, facilities, and/or instruments of execution that can comprise system 100 can include tablet computing devices, handheld devices, server class computing machines and/or devices/databases, laptop computers, notebook computers, desktop computers, cell phones, smart phones, consumer appliances and/or instrumentation, industrial devices and/or components, personal digital assistants, multimedia Internet enabled phones, multimedia players, and the like.

Moreover system 100, in addition to the illustrated components, engines, and devices, can additionally comprise, though not illustrated, multiple antenna groups, transmitter chains and/or receiver chains, which respectively can in turn comprise a plurality of components/devices associated with signal transmission and signal reception (e.g., processors, modulators, multiplexers, demodulators, demultiplexers, antennas, etc.), as will be appreciated by those skilled in the art.

As illustrated, system 100 can include sensitivity engine 102 that can be coupled to processor 104, memory 106, and storage 108. Sensitivity engine 102 can be in communication with processor 104 for facilitating operation of computer or machine executable instructions and/or components by sensitivity engine 102, memory 106 for storing data and/or the computer or machine executable instructions and/or components, and storage 108 for providing longer-term storage of the data and/or machine and/or computer executable instructions. Additionally, system 100 can also receive input 110 for use, manipulation, and/or transformation by sensitivity engine 102 to produce one or more useful, concrete, and tangible result and/or transform one or more articles to different states of things. Further, system 100 can produce, generate, and output the useful, concrete, and tangible results and/or the transformed one or more articles produced by sensitivity engine 102 and output as output 112.

In accordance with a disclosed embodiment, at the instigation of a user, sensitivity engine 102 can identify and select a sound frequency band within a defined scale, range, or spectrum of sound frequencies. Typically, the defined scale, range, or spectrum of sound frequencies can be within the audibility range of human hearing. On identifying and selecting a sound frequency band, sensitivity engine 102 can generate a sine tone representative of the sound frequency band (e.g., for ease of exposition, a center frequency associated with the sound frequency band) at a first intensity level (e.g., zero decibel or one decibel) and propagate the sine tone at the first intensity level, via wired and/or wireless signal transducers (e.g., headphones or headsets), to an auditory organ (e.g., ear) of the user.

Sensitivity engine 102 can thereafter incrementally and gradually increase the intensity level of the sine tone propagated through the wired and/or wireless signal transducers to the auditory organ of the user until the user indicates (e.g., by interacting the a graphical user interface displayed on a display device associated with system 100) that they have perceived the propagated sine tone at a second intensity level. The second intensity level can thus be recorded, for instance, in memory 106 and/or storage 108, as necessary and/or as required.

The selection of sound frequency bands within the defined spectrum or range of sound frequencies; generation of sine tones within the selected sound frequency bands of the defined spectrum or range of sound frequencies; propagation of the sine tones via the wired and/or wireless transducers to the auditory organ of the user; the incremental and gradual increase of the intensity levels associated with the propagated sine tone; and receiving indication from the user that they have perceived the propagated sine tone at a specific intensity level, can be repeated for all sound frequency bands within the defined spectrum or range of sound frequencies. It should be noted regard to the foregoing, that the foregoing acts are performed for one auditory organ of the user at any given time—the foregoing praxis therefore is not typically performed for both auditory organs of the user contemporaneously or simultaneously. Thus, once hearing sensitivity testing for a first auditory organ of the user has been completed, sensitivity engine 102 can repeat the foregoing process for the second auditory organ of the user.

Sensitivity engine 102, in response to determining that each auditory organ of the user has been tested, can thereafter generate auditory curves as a function of the results of the sensitivity tests conducted for each auditory organ of the user and as stored to memory 106 and/or storage 108. Sensitivity engine 102 can thereafter retrieve one or more auditory curves associated with hearing sensitivity levels typically linked with a defined demographic of users and as individuated for each auditory organ in the defined demographic from one of memory 106 and/or storage 108. Sensitivity engine 102 can then display the auditory curves determined as a function of the results of the sensitivity tests conducted for each auditory organ of the user superimposed over the one or more auditory curves associated with hearing sensitivity levels typically linked to a defined demographic group of users. The auditory curves can be displayed on a display device associated with system 100. Moreover, sensitivity engine 102, as a function of determining differences between the auditory curves generated and displayed for the user and the auditory curves associated with the defined demographic group of users, can, for example, display a request directed at the user that the user reduce the sound intensity output (e.g., output 112) by system 100.

Figure 2:
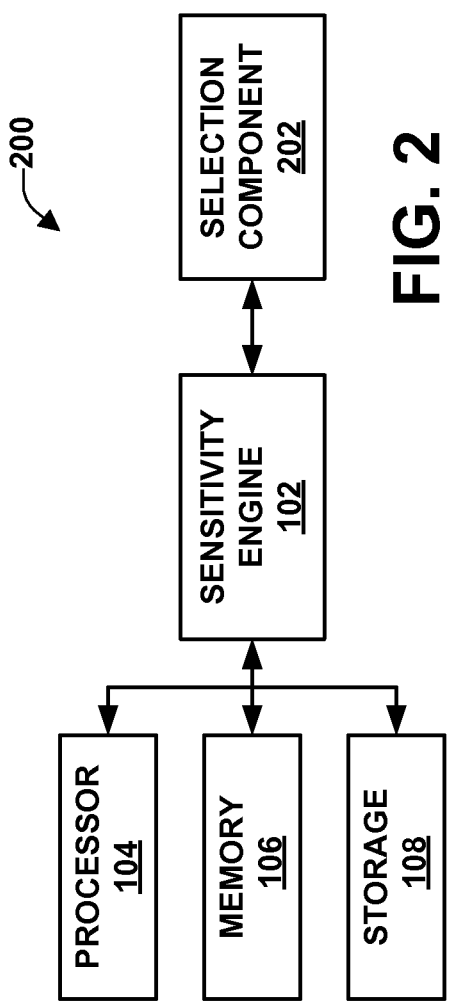
FIG. 2 illustrates an example non-limiting depiction of a system for hearing sensitivity testing and auto reinforcement, in accordance with various aspects and implementations described herein.

In regard to FIG. 2, illustrated is a further depiction of the devices, components, and engines that can comprise and augment the system for hearing sensitivity testing and auto reinforcement as described and depicted in FIG. 1. As illustrated in FIG. 2, the system 200 can include a selection component 202 in addition to sensitivity engine 102, processor 104, memory 106, and storage 108. In accordance with this aspect, selection component 202 can work in collaboration with sensitivity engine 102, processor 104, memory 106, and storage 108. Selection component 202 can determine, identify, and select a sound frequency band within a defined scale, range, or spectrum of sound frequencies. Generally, such a defined scale, range, or spectrum of sound frequencies will be in the audibility range of human hearing, e.g., typically between 20 Hz and 20,000 Hz. Further, selection component 202, in response to a user indicating that they have perceived a propagated sine tone in a first sound frequency band at a detectable intensity level, can identify and select a second or a successive other sound frequency band included in the defined scale, range, or spectrum of audible sound frequencies. Generally, selection component 202, for the purposes of hearing sensitivity testing and auto reinforcement, can identify and select a defined number of sound frequency bands, for instance eight sound frequency bands within the defined scale, range, or spectrum of sound frequencies can be identified and/or selected. Nevertheless, though eight sound frequency bands within the defined scale, range, or spectrum of sound frequencies has been disclosed, greater or lesser numbers of audible sound frequency bands within the defined scale, range, or spectrum of sound frequencies can be identified and selected by selection component 202.

Figure 3:
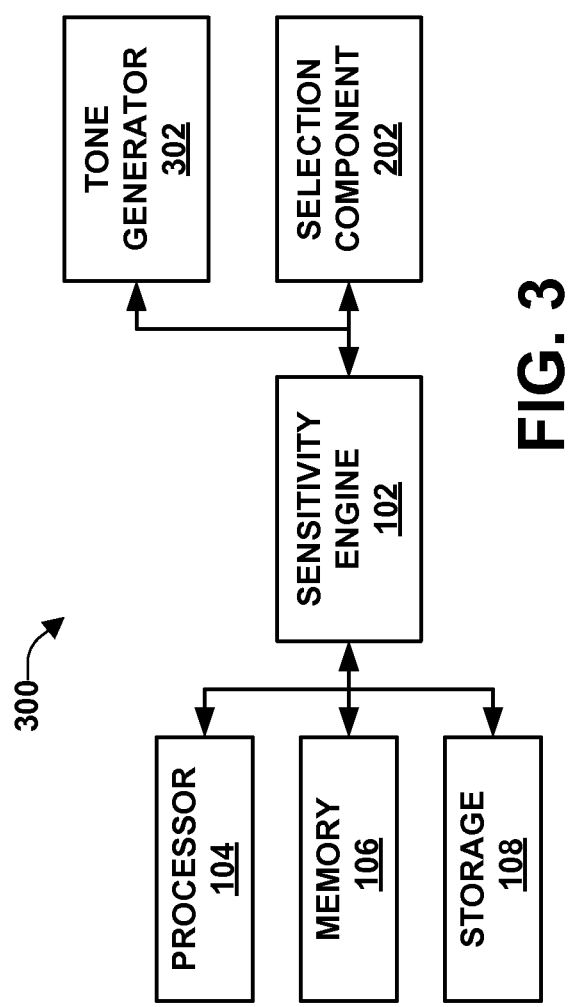
FIG. 3 illustrates an example non-limiting depiction of a further system for hearing sensitivity testing and auto reinforcement, in accordance with various aspects and implementations described herein.

With reference to FIG. 3, depicted therein are additional components, devices, and/or engines that can be included in a system for hearing sensitivity testing and auto reinforcement as described and illustrated in FIGS. 1-2. As illustrated in FIG. 3, the system for hearing sensitivity testing and auto reinforcement 300 can include tone generator 302. Tone generator 302 can operate in conjunction with sensitivity engine 102, processor 104, memory 106, storage 108, and selection component 202 to gradually and incrementally increase an intensity of the propagated sine tone identified and selected by selection component 202. In accordance with an aspect, tone generator 302 can commence generating the identified sine tone at a first intensity level (e.g., zero decibels) and thereafter can gradually and incrementally increase the intensity of the generated sine tone to a second intensity level, wherein the second intensity level is an intensity level at which the user perceives or recognizes, through wired and/or wireless headset or headphone devices, the generated and propagated sine tone. Tone generator 302 can provide this functionality for each and every selected sound frequency band within the defined scale, range, or spectrum of sound frequencies as identified and selected by selection component 202.

Figure 4:
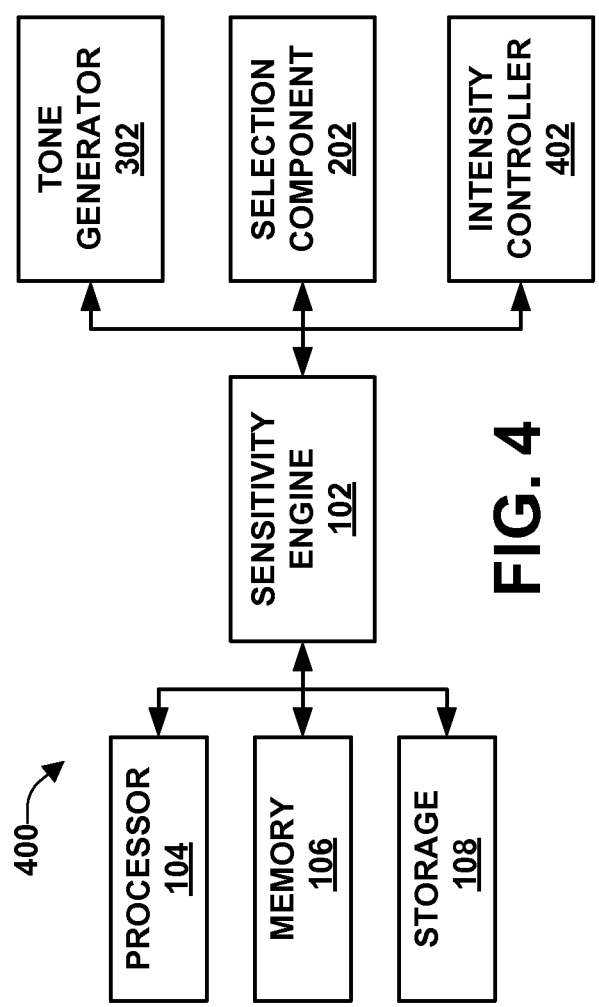
FIG. 4 illustrates an example non-limiting depiction of another system for hearing sensitivity testing and auto reinforcement, in accordance with various aspects and implementations described herein.

FIG. 4 provides further illustration of a system for hearing sensitivity testing and auto reinforcement, in accordance with an aspect. As depicted in FIG. 4, the system for hearing sensitivity testing and auto reinforcement 400, in addition to sensitivity engine 102, processor 104, memory 106, storage 108, selection component 202, and tone generator 302, can also include intensity controller 402. Intensity controller 402 can be responsible for gradually and incrementally increasing the intensity of a generated sine tone until an indication is received from a user that the generated and propagated sine tone has been perceived or recognized by the user. In accordance with an aspect, this indication or feedback can be received from the user when the user interacts with a graphical user interface displayed on a display device associated with the system.

Figure 5:
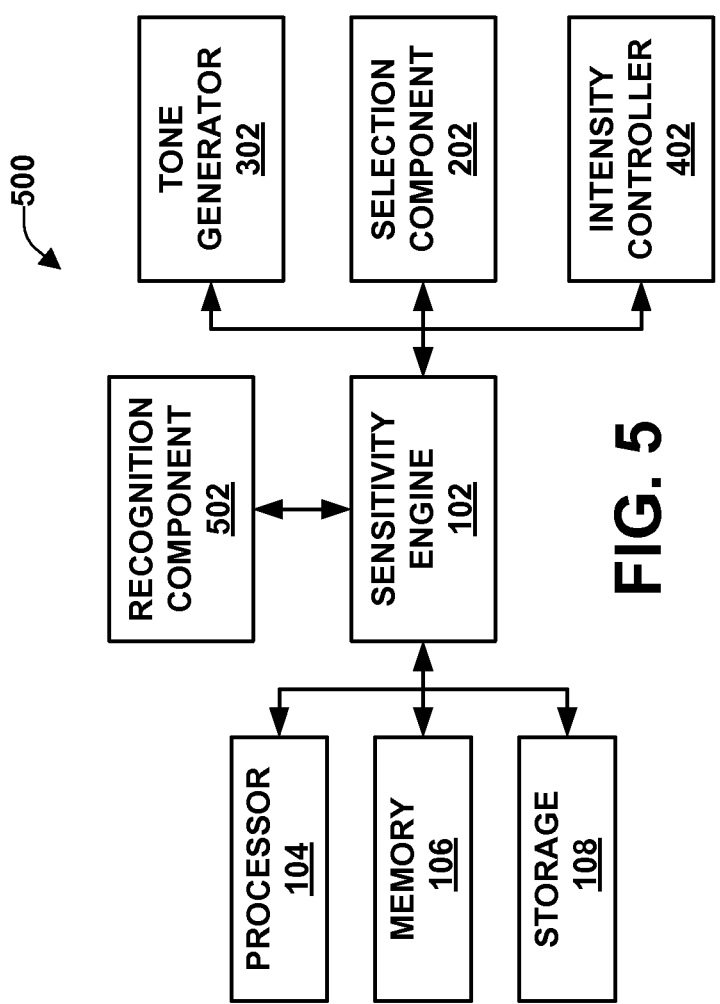
FIG. 5 illustrates an example non-limiting depiction system for hearing sensitivity testing and auto reinforcement, in accordance with various aspects and implementations described herein.

FIG. 5 provides additional illustration of the system for hearing sensitivity testing and auto reinforcement, in accordance with a further aspect. As illustrated in FIG. 5, the system for hearing sensitivity testing and auto reinforcement 500, in addition to sensitivity engine 102, processor 104, memory 106, storage 108, selection component 202, tone generator 302, and intensity controller 402, can also include recognition component 502. Recognition component 502 can be responsible for recognizing input from a graphical user interface displayed on a display device associated with the system. In accordance with an aspect, recognition component 502 can receive input from the graphical user interface when a user, on recognizing a generated and/or propagated sine tone at an intensity level, presses a button displayed in the graphical user interface.

Figure 6:
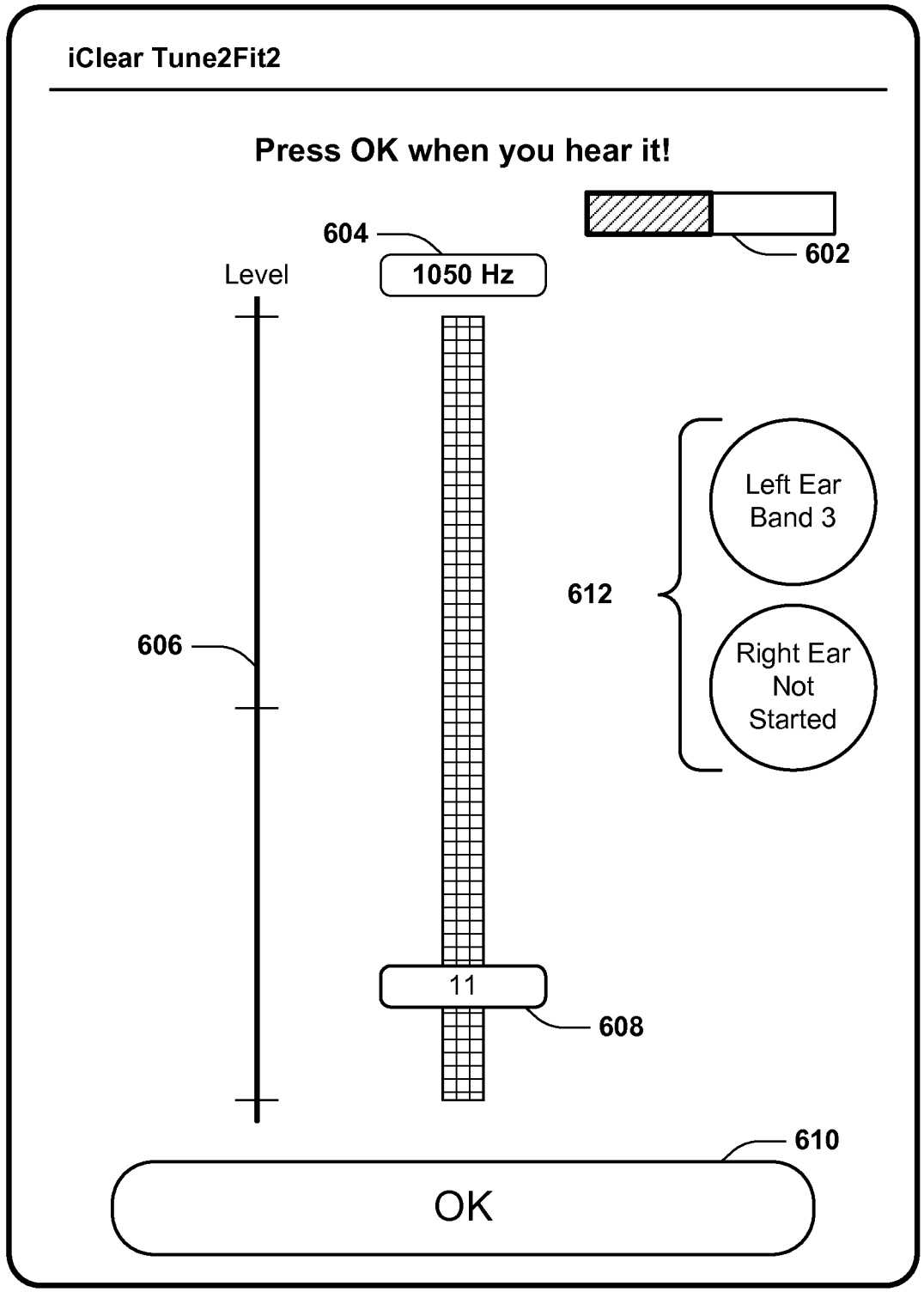
FIG. 6 illustrates an example non-limiting graphical user interface that facilitates hearing sensitivity testing and auto reinforcement, in accordance with various aspects and implementations described herein.

FIG. 6 illustrates a graphical user interface 600 in accordance with an embodiment. Graphical user interface 600, as depicted, can provide an instruction as to how to use the interface, e.g., "Press OK when you hear it!". Further, graphical user interface 600 can comprise a progress bar 602 that can show the completion or progress of the hearing sensitivity testing. Additionally, graphical user interface 600 can also include a current frequency indicator 604 that can indicate the frequency band that is currently being propagated through wirelessly and/or directly connected headset or headphone devices, a volume scale 606 that indicates volume intensity, for example, in decibels, and a volume slider bar 608 that displays a current volume intensity. The volume slider bar 608, in accordance with the disclosure, can also be utilized by a user of the apparatus, and graphical user interface 600, to adjust the volume intensity being output through connected wireless and/or wired audio signal transducers (e.g. wired/wireless headsets or headphones). Further, graphical user interface 600 can also include a button 610 that users can interact with when they perceive a propagated sine tone generated by tone generator 302 as adjusted for intensity by intensity controller 402. Additionally, graphical user interface 600 can provide indication as to the status of the respective auditory sensory organ that is being tested. For instance, as depicted as 612, a left ear status indicates that testing is currently in progress and is testing frequencies in audio band 3, whereas the right ear status indicates that right ear testing has still yet to commence.

In the context of the subject disclosure one or more further components (not shown) can be utilized and can aid in the various determinations and/or inferences upon which sensitivity engine 102, selection component 202, tone generator 302, intensity controller 402, and recognition component 502, etc. can rely. In an aspect, an inference component (not shown) can aid in the determination and selection of sound frequency bands with defined ranges, scales, or spectra of audible sound frequencies. In order to facilitate its aims, the inference component can examine the entirety or a subset of data to which it is granted access and can provide for reasoning about or inferring relevancy to and desirability of utilizing respective factors. The inference can be probabilistic—that is, the computation of a probability distribution over states of interest based on a consideration of data and events. An inference can also refer to techniques employed for composing higher-level events from a set of events or data.

Such inference can result in construction of new events or actions from a set of observed events or stored event data, whether or not the events are correlated in close temporal proximity, and whether the events and data come from one or several event and data sources. Various classifications (explicitly or implicitly trained) schemes or systems (e.g., support vector machines, neural networks, expert systems, Bayesian belief networks, fuzzy logic, data fusion engines, etc.) can be employed in connection with performing automatic or inferred action in connection with the claimed subject matter.

A classifier can map an input attribute vector, x=(x1, x2, x3, x4, xn), to a confidence that the input belongs to a class, such as by f(x)=confidence(class). Such classification can employ a probabilistic or statistical-based analysis (e.g., factoring into the analysis utilities and costs) to prognose or infer an action that a user desires to be automatically performed. A support vector machine (SVM) is an example of a classifier that can be employed. The SVM operates by finding a hyper-surface in the space of possible inputs, where the hyper-surface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, and probabilistic classification models providing different patterns of independence can be employed. Classification as used in this disclosure also is inclusive of statistical regression that is utilized to develop models of priority.

Figure 7:
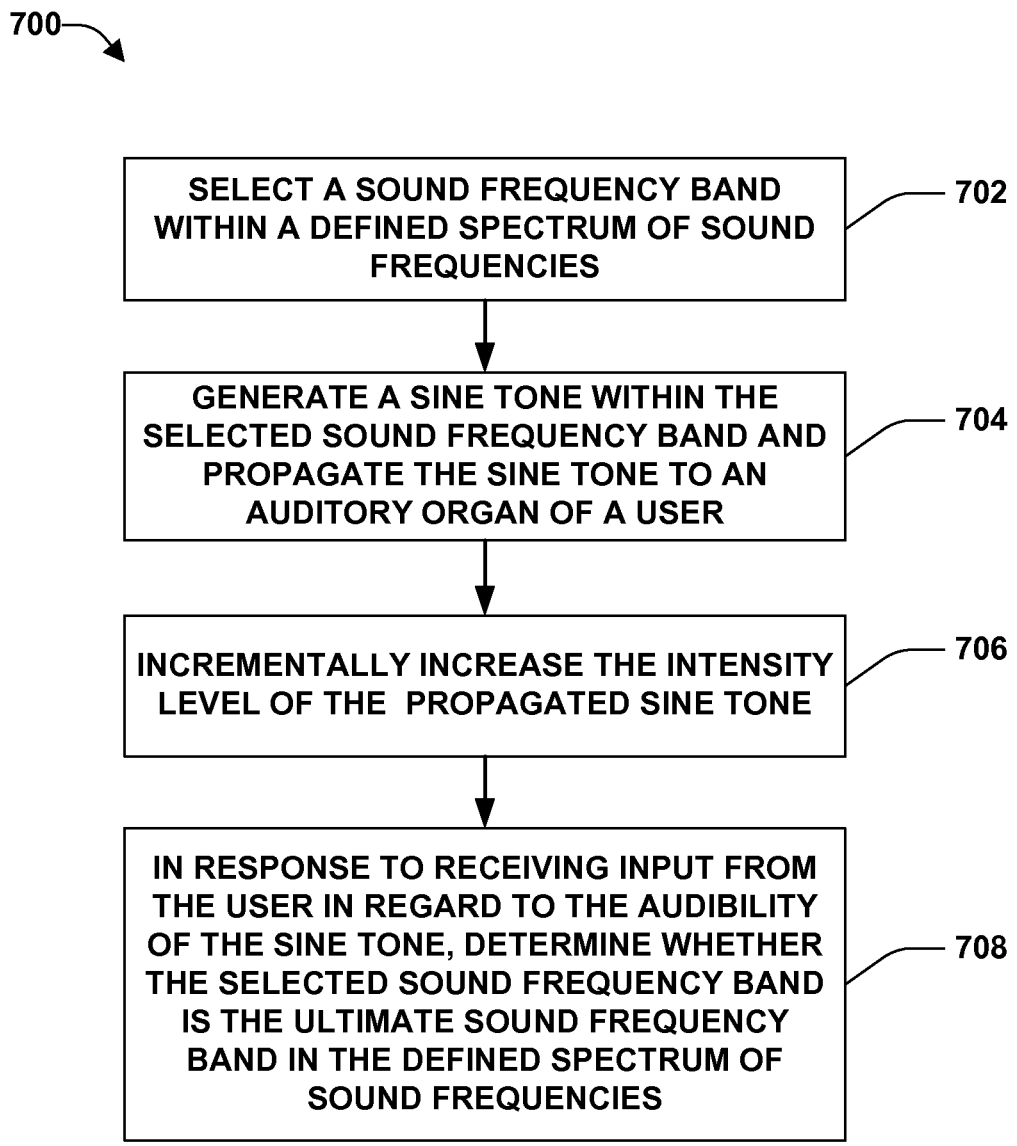
FIG. 7 illustrates an example methodology for hearing sensitivity testing and auto reinforcement, in accordance with various aspects and implementations described herein.
Figure 8:
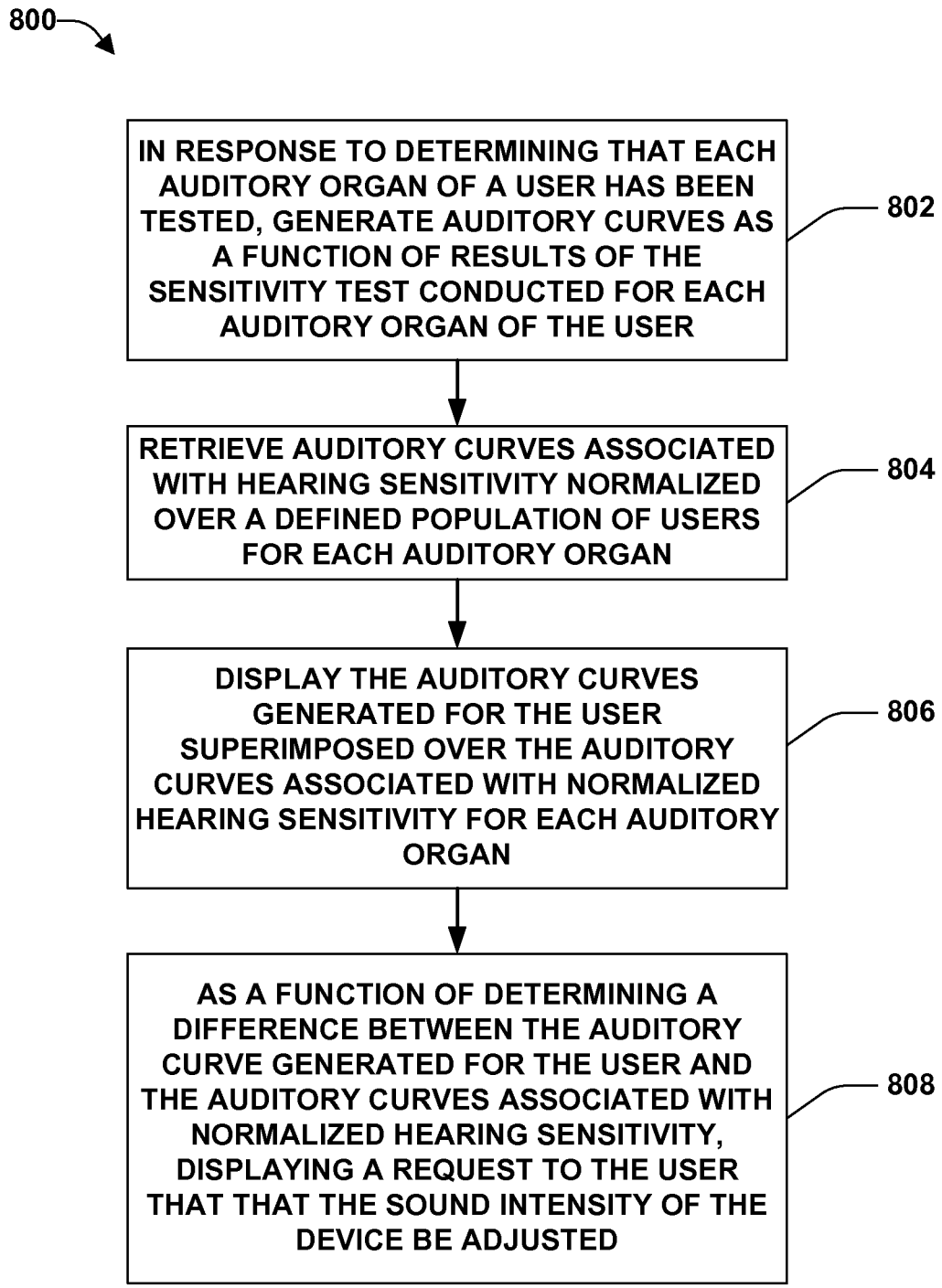
FIG. 8 illustrates an example methodology for hearing sensitivity testing and auto reinforcement, in accordance with various aspects and implementations described herein.

FIGS. 7-8 illustrate methodologies or flow diagrams in accordance with certain aspects of this disclosure. While, for purposes of simplicity of explanation, the methodologies are shown and described as a series of acts, the disclosed subject matter is not limited by the order of acts, as some acts may occur in different orders and/or concurrently with other acts from that shown and described herein. For example, those skilled in the art will understand and appreciate that a methodology can alternatively be represented as a series of interrelated states or events, such as in a state diagram. Moreover, not all illustrated acts may be required to implement a methodology in accordance with the disclosed subject matter. Additionally, it is to be appreciated that the methodologies disclosed in this disclosure are capable of being stored on an article of manufacture to facilitate transporting and transferring such methodologies to computers, machined, or other devices comprising processors and/or memories or storage devices.

Referring now to FIG. 7, presented is a flow diagram of an example method 700 for hearing sensitivity testing and auto reinforcement. Method 700 can commence at 702 where a sound frequency band within a defined spectrum or range of sound frequencies can be selected. At 704, a sine tone within the selected sound frequency band can be generated and propagated to a first auditory organ of a user via audio signal transducers, such as wired/wireless headsets or headphones. At act 706, the sine tone that is being generated and propagated to the first auditory organ of the user via the wired/wireless audio signal transducers can be incrementally and gradually increased in volume intensity level. At 708, in response to receiving input from a user in regard to the audibility of the propagated and generated sine tone, a determination can be made as to whether the selected sound frequency band within the defined spectrum or range of sound frequencies is the ultimate sound frequency band. If it is ascertained that the sound frequency band is the ultimate sound frequency band in the defined spectrum of sound frequencies, it can be assumed that testing for the auditory organ of the user has been completed and that, if necessary, testing of the second auditory organ of the user can commence.

Referring now to FIG. 8, presented is a flow diagram of another example method 800 for hearing sensitivity testing and auto reinforcement. Once hearing sensitivity testing for each auditory organ of the user has been completed, method 800 can commence at act 802, wherein in response to determining that each auditory organ of the user has been tested, auditory curves can be generated as a function of the results of the sensitivity tests conducted for each of the auditory organs of the user. At 804, auditory curves associated with hearing sensitivity normalized over a defined or definable population group or demographic of users can be retrieved from a storage medium (e.g., memory 106 and/or storage 108). At 806 the auditory curves generated for the user for each ear can be superimposed over the auditory curves associated with the normalized hearing sensitivities for a defined demographic and for each ear can be displayed on a display device. At 808, a notification can be presented on the display device indicating to the user that the volume intensity level of the device should be adjusted downwards to prevent further hearing loss. The notification can be generated as a function of determining a difference between auditory curves generated for the user and the auditory curves generated and associated with the normalized hearing sensitivities for the defined demographic and for each ear of the defined demographic.

In view of the exemplary systems described above, methodologies that may be implemented in accordance with the described subject matter will be better appreciated with reference to the flowcharts of the various figures. While for purposes of simplicity of explanation, the methodologies are shown and described as a series of blocks, it is to be understood and appreciated that the claimed subject matter is not limited by the order of the blocks, as some blocks may occur in different orders and/or concurrently with other blocks from what is depicted and described in this disclosure. Where non-sequential, or branched, flow is illustrated via flowchart, it can be appreciated that various other branches, flow paths, and orders of the blocks, may be implemented which achieve the same or a similar result. Moreover, not all illustrated blocks may be required to implement the methodologies described hereinafter.

In addition to the various aspects described in this disclosure, it is to be understood that other similar aspects can be used or modifications and additions can be made to the described aspect(s) for performing the same or equivalent function of the corresponding aspect(s) without deviating there from. Still further, multiple processing chips or multiple devices can share the performance of one or more functions described in this disclosure, and similarly, storage can be effected across a plurality of devices. Accordingly, the invention is not to be limited to any single aspect, but rather can be construed in breadth, spirit and scope in accordance with the appended claims.

Example Operating Environments

The systems and processes described below can be embodied within hardware, such as a single integrated circuit (IC) chip, multiple ICs, an application specific integrated circuit (ASIC), or the like. Further, the order in which some or all of the process blocks appear in each process should not be deemed limiting. Rather, it should be understood that some of the process blocks can be executed in a variety of orders, not all of which may be explicitly illustrated in this disclosure.

Figure 9:
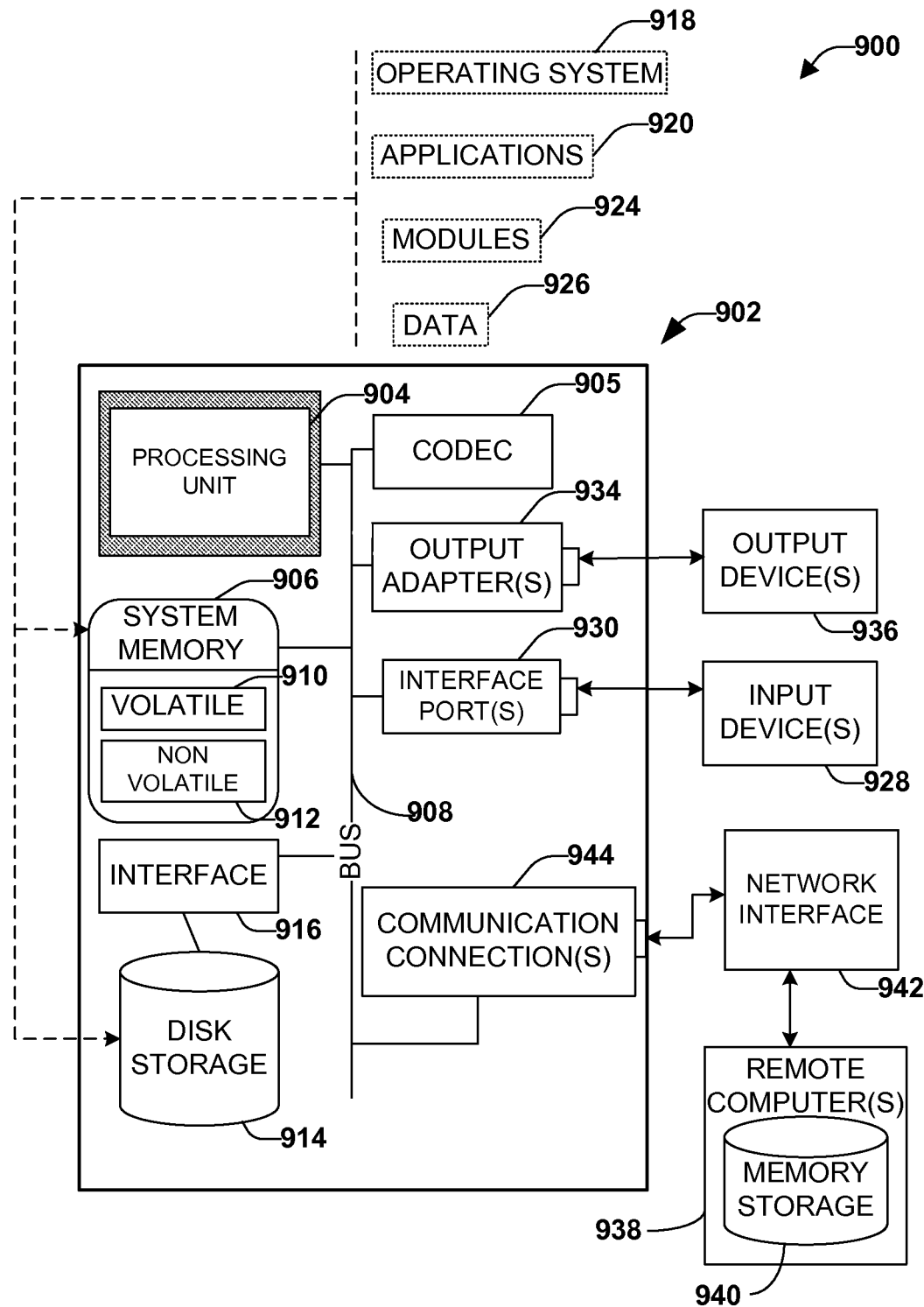
FIG. 9 is a block diagram representing an exemplary non-limiting networked environment in which various aspects can be implemented.

With reference to FIG. 9, a suitable environment 900 for implementing various aspects of the claimed subject matter includes a computer or computing device 902. The computer or computing device 902 includes a processing unit 904, a system memory 906, a codec 905, and a system bus 908. In an aspect, processing unit 904 and system memory 906 can represent processor 104, and memory 106 respectively. The system bus 908 couples system components including, but not limited to, the system memory 906 to the processing unit 904. The processing unit 904 can be any of various available processors. Dual microprocessors and other multiprocessor architectures also can be employed as the processing unit 904.

The system bus 908 can be any of several types of bus structure(s) including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCMCIA), Firewire (IEEE 13184), and Small Computer Systems Interface (SCSI).

The system memory 906 includes volatile memory 910 and non-volatile memory 912. The basic input/output system (BIOS), containing the basic routines to transfer information between elements within the computer or computing device 902, such as during start-up, is stored in non-volatile memory 912. In addition, according to present disclosure, codec 905 may include at least one of an encoder or decoder, wherein the at least one of an encoder or decoder may consist of hardware, a combination of hardware and software, or software. Although, codec 905 is depicted as a separate component, codec 905 may be contained within non-volatile memory 912. By way of illustration, and not limitation, non-volatile memory 912 can include read only memory (ROM), programmable ROM (PROM), electrically programmable ROM (EPROM), electrically erasable programmable ROM (EEPROM), or flash memory. Volatile memory 910 includes random access memory (RAM), which acts as external cache memory. According to present aspects, the volatile memory may store the write operation retry logic (not shown in FIG. 9) and the like. By way of illustration and not limitation, RAM is available in many forms such as static RAM (SRAM), dynamic RAM (DRAM), synchronous DRAM (SDRAM), double data rate SDRAM (DDR SDRAM), and enhanced SDRAM (ES-DRAM).

Computer or computing device 902 may also include removable/non-removable, volatile/non-volatile computer storage medium. FIG. 9 illustrates, for example, disk storage 914. Disk storage 914 includes, but is not limited to, devices like a magnetic disk drive, solid state disk (SSD) floppy disk drive, tape drive, Jaz drive, Zip drive, LS-70 drive, flash memory card, or memory stick. In addition, disk storage 914 can include storage medium separately or in combination with other storage medium including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage devices 914 to the system bus 908, a removable or non-removable interface is typically used, such as interface 916.

It is to be appreciated that FIG. 9 describes software that acts as an intermediary between users and the basic computer resources described in the suitable operating environment 900. Such software includes an operating system 910. Operating system 910, which can be stored on disk storage 914, acts to control and allocate resources of the computer system 902. Applications 920 take advantage of the management of resources by operating system 718 through program modules 924, and program data 926, such as the boot/shutdown transaction table and the like, stored either in system memory 906 or on disk storage 914. It is to be appreciated that the claimed subject matter can be implemented with various operating systems or combinations of operating systems.

A user enters commands or information into the computer or computing device 902 through input device(s) 928. Input devices 928 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 904 through the system bus 908 via interface port(s) 930. Interface port(s) 930 include, for example, a serial port, a parallel port, a game port, and a universal serial bus (USB). Output device(s) 936 use some of the same type of ports as input device(s) 928. Thus, for example, a USB port may be used to provide input to computer or computing device 902, and to output information from computer or computing device 902 to an output device 936. Output adapter 934 is provided to illustrate that there are some output devices 936 like monitors, speakers, and printers, among other output devices 936, which require special adapters. The output adapters 934 include, by way of illustration and not limitation, video and sound cards that provide a means of connection between the output device 936 and the system bus 908. It should be noted that other devices and/or systems of devices provide both input and output capabilities such as remote computer(s) 938.

Computer or computing device 902 can operate in a networked environment using logical connections to one or more remote computers, such as remote computer(s) 938. The remote computer(s) 938 can be a personal computer, a server, a router, a network PC, a workstation, a microprocessor based appliance, a peer device, a smart phone, a tablet, or other network node, and typically includes many of the elements described relative to computer or computing device 902. For purposes of brevity, only a memory storage device 940 is illustrated with remote computer(s) 938. Remote computer(s) 938 is logically connected to computer or computing device 902 through a network interface 942 and then connected via communication connection(s) 944. Network interface 942 encompasses wire and/or wireless communication networks such as local-area networks (LAN) and wide-area networks (WAN) and cellular networks. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 944 refers to the hardware/software employed to connect the network interface 942 to the bus 908. While communication connection 944 is shown for illustrative clarity inside computer or computing device 902, it can also be external to computer or computing device 902. The hardware/software necessary for connection to the network interface 942 includes, for exemplary purposes only, internal and external technologies such as, modems including regular telephone grade modems, cable modems and DSL modems, ISDN adapters, and wired and wireless Ethernet cards, hubs, and routers.

Figure 10:
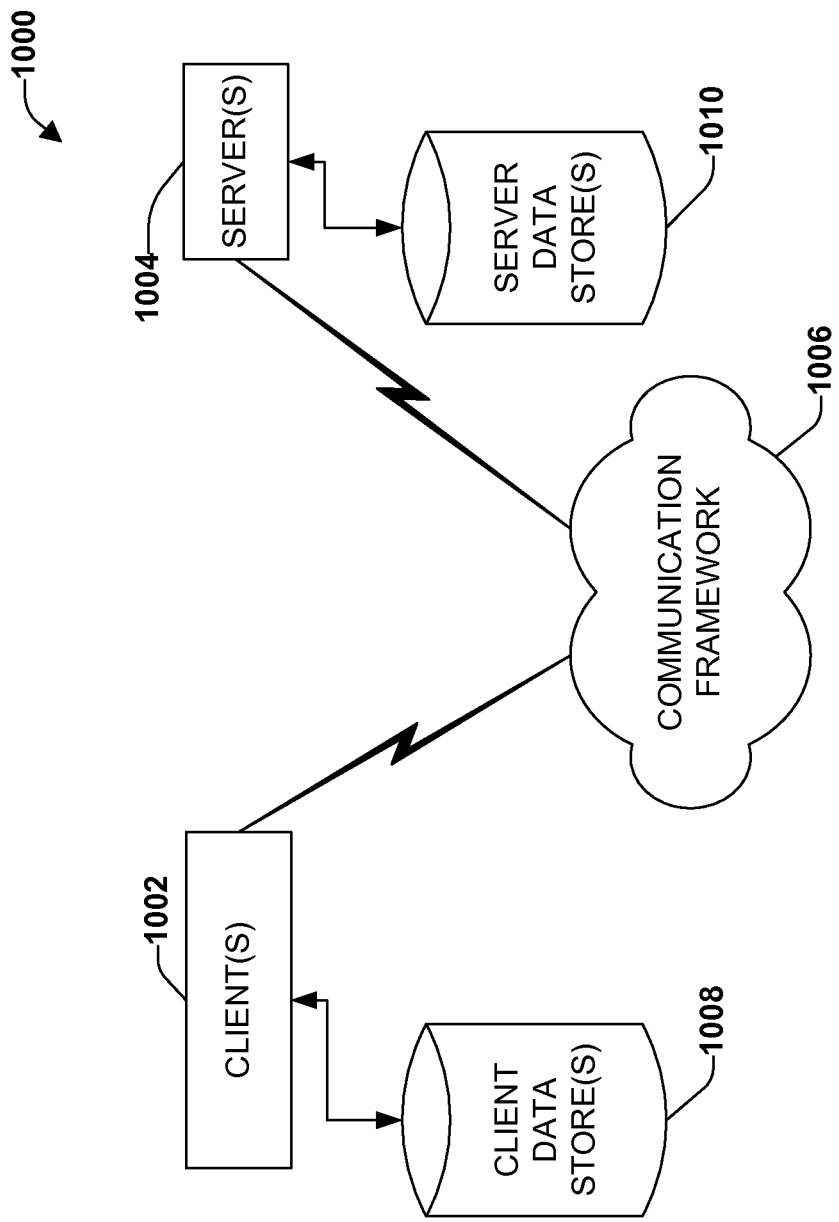
FIG. 10 is a block diagram representing an exemplary non-limiting computing system or operating environment in which various aspects may be implemented.

Referring now to FIG. 10, there is illustrated a schematic block diagram of a computing environment 1000 in accordance with this disclosure. System 1000 can for example be employed in connection with implementing one or more of the systems or components described herein and shown FIGS. 1-5. The system 1000 includes one or more client(s) 1002 (e.g., laptops, smart phones, PDAs, media players, computers, portable electronic devices, tablets, and the like). The client(s) 1002 can be hardware and/or software (e.g., threads, processes, computing devices). The system 1000 also includes one or more server(s) 1004. The server(s) 1004 can also be hardware or hardware in combination with software (e.g., threads, processes, computing devices). The servers 1004 can house threads to perform transformations by employing aspects of this disclosure, for example. One possible communication between a client 1002 and a server 1004 can be in the form of a data packet transmitted between two or more computer processes wherein the data packet may include video data. The data packet can include metadata, e.g., associated contextual information, for example. The system 1000 includes a communication framework 1006 (e.g., a global communication network such as the Internet, or mobile network(s)) that can be employed to facilitate communications between the client(s) 1002 and the server(s) 1004.

Communications can be facilitated via a wired (including optical fiber) and/or wireless technology. The client(s) 1002 include or are operatively connected to one or more client data store(s) 1008 that can be employed to store information local to the client(s) 1002 (e.g., associated contextual information). Similarly, the server(s) 1004 are operatively include or are operatively connected to one or more server data store(s) 1010 that can be employed to store information local to the servers 1004.

In one aspect, a client 1002 can transfer an encoded file, in accordance with the disclosed subject matter, to server 1004. Server 1004 can store the file, decode the file, or transmit the file to another client 1002. It is to be appreciated, that a client 1002 can also transfer uncompressed file to a server 1004 and server 1004 can compress the file in accordance with the disclosed subject matter. Likewise, server 1004 can encode video information and transmit the information via communication framework 1006 to one or more clients 1002.

The illustrated aspects of the disclosure may also be practiced in distributed computing environments where certain tasks are performed by remote processing devices that are linked through a communications network. In a distributed computing environment, program modules can be located in both local and remote memory storage devices.

Moreover, it is to be appreciated that various components described in this description can include electrical circuit(s) that can include components and circuitry elements of suitable value in order to implement the aspects of the subject disclosure(s). Furthermore, it can be appreciated that many of the various components can be implemented on one or more integrated circuit (IC) chips. For example, in one aspect, a set of components can be implemented in a single IC chip. In other aspects, one or more of respective components are fabricated or implemented on separate IC chips.

What has been described above includes examples of the aspects of the present invention. It is, of course, not possible to describe every conceivable combination of components or methodologies for purposes of describing the claimed subject matter, but it is to be appreciated that many further combinations and permutations of the subject disclosure are possible. Accordingly, the claimed subject matter is intended to embrace all such alterations, modifications, and variations that fall within the spirit and scope of the appended claims. Moreover, the above description of illustrated aspects of the subject disclosure, including what is described in the Abstract, is not intended to be exhaustive or to limit the disclosed aspects to the precise forms disclosed. While specific aspects and examples are described in this disclosure for illustrative purposes, various modifications are possible that are considered within the scope of such aspects and examples, as those skilled in the relevant art can recognize.

In particular and in regard to the various functions performed by the above described components, devices, circuits, systems and the like, the terms used to describe such components are intended to correspond, unless otherwise indicated, to any component which performs the specified function of the described component (e.g., a functional equivalent), even though not structurally equivalent to the disclosed structure, which performs the function in the disclosure illustrated exemplary aspects of the claimed subject matter. In this regard, it will also be recognized that the subject disclosure includes a system as well as a computer-readable storage medium having computer-executable instructions for performing the acts and/or events of the various methods of the claimed subject matter.

The aforementioned systems/circuits/modules have been described with respect to interaction between several components/blocks. It can be appreciated that such systems/circuits and components/blocks can include those components or specified sub-components, some of the specified components or sub-components, and/or additional components, and according to various permutations and combinations of the foregoing. Sub-components can also be implemented as components communicatively coupled to other components rather than included within parent components (hierarchical). Additionally, it should be noted that one or more components may be combined into a single component providing aggregate functionality or divided into several separate sub-components, and any one or more middle layers, such as a management layer, may be provided to communicatively couple to such sub-components in order to provide integrated functionality. Any components described in this disclosure may also interact with one or more other components not specifically described in this disclosure but known by those of skill in the art.

In addition, while a particular feature of the subject disclosure may have been disclosed with respect to only one of several implementations, such feature may be combined with one or more other features of the other implementations as may be desired and advantageous for any given or particular disclosure. Furthermore, to the extent that the terms "includes," "including," "has," "contains," variants thereof, and other similar words are used in either the detailed description or the claims, these terms are intended to be inclusive in a manner similar to the term "comprising" as an open transition word without precluding any additional or other elements.

As used in this disclosure, the terms "component," "module," "system," or the like are generally intended to refer to a computer-related entity, either hardware (e.g., a circuit), a combination of hardware and software, software, or an entity related to an operational machine with one or more specific functionalities. For example, a component may be, but is not limited to being, a process running on a processor (e.g., digital signal processor), a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers. Further, a "device" can come in the form of specially designed hardware; generalized hardware made specialized by the execution of software thereon that enables the hardware to perform specific function; software stored on a computer readable storage medium; software transmitted on a computer readable transmission medium; or a combination thereof.

Moreover, the words "example" or "exemplary" are used in this disclosure to mean serving as an example, instance, or illustration. Any aspect or design described in this disclosure as "exemplary" is not necessarily to be construed as preferred or advantageous over other aspects or designs. Rather, use of the words "example" or "exemplary" is intended to present concepts in a concrete fashion. As used in this disclosure, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this disclosure and the appended claims should generally be construed to mean "one or more" unless specified otherwise or clear from context to be directed to a singular form.

Computing devices typically include a variety of media, which can include computer-readable storage media and/or communications media, in which these two terms are used in this description differently from one another as follows. Computer-readable storage media can be any available storage media that can be accessed by the computer, is typically of a non-transitory nature, and can include both volatile and nonvolatile media, removable and non-removable media. By way of example, and not limitation, computer-readable storage media can be implemented in connection with any method or technology for storage of information such as computer-readable instructions, program modules, structured data, or unstructured data. Computer-readable storage media can include, but are not limited to, RAM, ROM, EEPROM, flash memory or other memory technology, CD ROM, digital versatile disk (DVD) or other optical disk storage, magnetic cassettes, magnetic tape, magnetic disk storage or other magnetic storage devices, or other tangible and/or non-transitory media which can be used to store desired information. Computer-readable storage media can be accessed by one or more local or remote computing devices, e.g., via access requests, queries or other data retrieval protocols, for a variety of operations with respect to the information stored by the medium.

On the other hand, communications media typically embody computer-readable instructions, data structures, program modules or other structured or unstructured data in a data signal that can be transitory such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

In view of the exemplary systems described above, methodologies that may be implemented in accordance with the described subject matter will be better appreciated with reference to the flowcharts of the various figures. For simplicity of explanation, the methodologies are depicted and described as a series of acts. However, acts in accordance with this disclosure can occur in various orders and/or concurrently, and with other acts not presented and described in this disclosure. Furthermore, not all illustrated acts may be required to implement the methodologies in accordance with certain aspects of this disclosure. In addition, those skilled in the art will understand and appreciate that the methodologies could alternatively be represented as a series of interrelated states via a state diagram or events. Additionally, it should be appreciated that the methodologies disclosed in this disclosure are capable of being stored on an article of manufacture to facilitate transporting and transferring such methodologies to computing devices. The term article of manufacture, as used in this disclosure, is intended to encompass a computer program accessible from any computer-readable device or storage media.

What is claimed is:

1. A device, comprising:
a processor; and
a memory that stores executable instructions that, when executed by the processor, facilitate performance of operations, comprising:
as a function of an identified demographic of users and an application of a probability distribution to the identified demographic of users, generating a first sine tone representing a first audible frequency within a defined band of audible frequencies;
propagating the first sine tone to a first auditory organ of a user of the users;
in response to receiving input from the user, determining a minimum intensity of the first sine tone recognized by the user;
as a function of the minimum intensity of the first sine tone, determining a set of parameters representative of a hearing response of the user;
based on the hearing response of the user, generating a hearing curve of a grouping of normalized hearing curves for the identified demographic of users, wherein the generation comprises a model classification approach employed to aid in selection of one or more sound frequency bands having defined ranges, scales, or spectra of audible sound frequencies; and
as a function of the grouping of normalized hearing curves and a statistical based utility analysis that determines that a utility associated with adjusting a filter of a hearing aid device is greater than a cost associated with adjusting the filter of the hearing aid device, facilitating the adjusting of the filter.

2. The device of claim 1, the operations further comprising incrementally increasing an intensity of the first sine tone until the user indicates recognition of the first sine tone.

3. The device of claim 1, wherein the first sine tone represents a center frequency in the defined band of audible frequencies.

4. The device of claim 1, the operations further comprising propagating the first sine tone to a second auditory organ of the user.

5. The device of claim 4, wherein the first auditory organ of the user is a right ear and the second auditory organ of the user is a left ear.

6. The device of claim 1, the operations further comprising generating a second sine tone representing a second audible frequency in the defined band of audible frequencies.

7. The device of claim 6, the operations further comprising propagating the second sine tone to the first auditory organ of the user.

8. The device of claim 6, the operations further comprising propagating the second sine tone to a second auditory organ of the user.

9. The device of claim 1, wherein the defined band is a first defined band, the operations further comprising, in response to receiving input from the user, generating a third sine tone representing a third audible frequency in a second defined band of audible frequencies.

10. The device of claim 9, the operations further comprising propagating the third sine tone to the first auditory organ of the user.

11. The device of claim 9, the operations further comprising propagating the third sine tone to a second auditory organ of the user.

12. The device of claim 1, the operations further comprising as a function receiving responses from the user for sine tones representing audible frequencies comprising a set of defined bands of audible frequencies for the first auditory organ, determining a set of parameters representing respective signal levels and gain settings for the set of defined bands of audible frequencies.

13. A method, comprising:
based on an inference determined as a function of an identified demographic of users and an application of a probability distribution curve to the identified demographic of users, generating, by a system comprising a processor, a first sine tone representing an audible frequency;
propagating, by the system, the first sine tone to a first sound sensor of a user;
increasing, by the system, an intensity level of the first sine tone from a first intensity level to a second intensity level;
as a function of the second intensity level, determining, by the system, for the first sound sensor of the user, a set of parameters representing respective signal levels or respective gain settings for sine tones representing audible frequencies in a defined band of frequencies;
based on the set of parameters, generating, by the system, a hearing curve of a grouping of normalized hearing curves for the identified demographic of users, wherein the generating comprises employing a model classification approach to aid in selection of one or more sound frequency bands having defined ranges, scales, or spectra of audible sound frequencies; and
as a function of the grouping of normalized hearing curves and a determination, based on a probabilistic based analysis, that a utility of adjusting a filter of a hearing aid device exceeds a cost of the adjusting the filter of the hearing aid device, facilitating, by the system, the adjusting of the filter of the hearing aid device.

14. The method of claim 13, wherein the second intensity level is the intensity level of the first sine tone that the user is determined to have recognized as being perceptible.

15. The method of claim 13, wherein the first sine tone represents a center frequency in the audible frequency.

16. The method of claim 13, further comprising:
after the first sine tone has been propagated to the first sound sensor of the user, generating, by the system, a second sine tone representing another audible frequency;
propagating, by the system, the second sine tone to a second sound sensor of a user;
increasing, by the system, an intensity level of the second sine tone from a third intensity level to a fourth intensity level; and
as a function of the fourth intensity level, determining, by the system, for the second sound sensor of the user, another set of parameters representing respective other signal levels or respective other gain settings for other sine tones representing other audible frequencies in another defined band of frequencies.

17. A non-transitory machine-readable medium, comprising executable instructions that, when executed by a processor, facilitate performance of operations, comprising:
in response to an inference determined as a function of an identified demographic of users and an application of a probability distribution to the identified demographic of users, generating a first sine tone representing an audible frequency;

propagating the first sine tone, via a first electro-acoustic transducer, to a first ear associated with a user identity;

increasing an intensity level of the first sine tone, supplied via the electro-acoustic transducer to the first ear, from a first intensity level to a second intensity level;

determining, for the first ear of the user and as a function of the second intensity level, parameters representing a signal level or a gain setting for each sine tone representing each audible frequency in a defined band of frequencies;

based on the parameters, generating normalized hearing curve data representative of a group of normalized hearing curves for the identified demographic of users, wherein the generating comprises employing a model classification approach to aid in selection of one or more sound frequency bands having defined ranges, scales, or spectra of audible sound frequencies; and as a function of the normalized hearing curve data and as a function of determining that a cost associated with not adjusting a filter associated with a hearing aid device exceeds a utility associated with adjusting the filter associated with the hearing aid device, facilitating the adjusting of the filter.

18. The non-transitory machine-readable medium of claim 17, the operations further comprising:

after each sine tone representing each audible frequency in the defined band of frequencies has been propagated to the first ear of the user, generating a third sine tone representing another audible frequency;

propagating the third sine tone, via a second electro-acoustic transducer, to a second ear associated with the user identity;

increasing, by the system, another intensity level of a second sine tone from a third intensity level to a fourth intensity level; and determining, for the second ear associated with the user identity and as a function of the fourth intensity level, other parameters representing another signal level or another gain setting for each other sine tone representing each other audible frequency in another defined band of frequencies.

19. The non-transitory machine-readable medium of claim 18, wherein the first ear is a right ear.

20. The non-transitory machine-readable medium of claim 18, wherein the second ear is a left ear.

\* \* \* \* \*